United States Patent [19]

Anderson et al.

[11] Patent Number: 5,639,803

[45] Date of Patent: Jun. 17, 1997

[54] PROCESS FOR INCORPORATING BIOCIDES INTO A LIQUID DISPERSION

[75] Inventors: Bruce Beardsley Anderson, Guilford; Rahim Hani, Cheshire, both of Conn.

[73] Assignee: Olin Corporation, Cheshire, Conn.

[21] Appl. No.: 747,076

[22] Filed: Aug. 19, 1991

Related U.S. Application Data

[63] Continuation-in-part of Ser. No. 600,476, Oct. 19, 1990, abandoned.

[51] Int. Cl.$^6$ .................................................... C08K 5/12
[52] U.S. Cl. ................................................. 523/122; 524/99
[58] Field of Search .................................. 523/122; 524/99

[56] References Cited

U.S. PATENT DOCUMENTS

| | | | |
|---|---|---|---|
| 3,755,224 | 8/1973 | Lutz | 523/122 |
| 4,049,822 | 9/1977 | Rei et al. | 523/122 |
| 4,086,297 | 4/1978 | Rei et al. | 260/859 |
| 4,631,301 | 12/1986 | Kozuma et al. | 523/122 |
| 4,661,528 | 4/1987 | Rei | 523/122 |
| 4,663,359 | 5/1987 | Rei | 521/85 |
| 4,683,080 | 7/1987 | Rei et al. | 523/122 |
| 4,789,692 | 12/1988 | Rei et al. | 523/122 |
| 5,102,657 | 4/1992 | Rei et al. | 523/122 |
| 5,319,000 | 6/1994 | O'Conner et al. | 523/122 |

*Primary Examiner*—Ralph H. Dean
*Attorney, Agent, or Firm*—Dale Lynn Carlson; Wiggin & Dana

[57] ABSTRACT

This invention relates to a multi-step process for preparing a storage-stable dispersion of a biocide which comprises the steps of: (a) contacting a heat-swellable resin with a carrier to provide a liquid mixture of a resin and a carrier, (b) heating said liquid mixture to an elevated temperature to cause the resin to swell by virtue of carrier absorption into the resin to provide a swelled resin in said liquid mixture, and (c) adding a biocide to said swelled resin and mixing to provide a homogeneous, storage-stable liquid dispersion.

5 Claims, No Drawings

PROCESS FOR INCORPORATING BIOCIDES INTO A LIQUID DISPERSION

This application is a continuation-in-part of application Ser. No. 07/600,476, filed Oct. 19, 1990, now abandoned.

FIELD OF THE INVENTION

The present invention relates generally to a delivery system for polymer additives, and, more specifically, to a process for providing physically stable dispersions of a biocide in a polymer resin composition.

BACKGROUND OF THE INVENTION

Various methods for incorporating biocides into resin compositions have been disclosed in the prior art. By way of illustration, U.S. Pat. No. 4,086,297 discloses a process for forming a solid thermoplastic composition containing a microbiocide utilizing very high levels of the microbiocide and two thermoplastic resins in conjunction with melt blending processing.

As another illustration, U.S. Pat. No. 4,663,359 discloses a process for preparing a microbiocide concentrate which is useful in plastisol systems. The process comprises mixing a porous thermoplastic resin powder with a high concentration of microbiocide at an elevated temperature sufficient to melt the biocide and open the pores of the resin, and incorporating the melted biocide into the pores of the porous resin, optionally in the presence of a carrier. The resulting product is provided as a dry, free-flowing powder containing the microbiocide in a high concentration at least about 20 times greater than the normal upper usage concentration for the microbiocide.

Unfortunately, the products produced in accordance with the above-mentioned '297 and '395 patents are solids which are frequently more difficult to process into a finished product than might be desired. Liquid dispersions would avoid such solids handling problems in subsequent processing steps. Heretofore, however, suitable methods for incorporating insoluble or difficult-to-solubilize additives, such as biocides, into liquid dispersions has represented a challenge to the plastics manufacturing community. The solids in such liquid dispersions tend to settle out over time, thus causing a non-uniform distribution of the additive in the dispersion. In addition, certain liquid dispersions, most notably plastisols, tend to increase in viscosity with increasing temperature, thus posing a risk that the dispersion will "set-up" or solidify during storage and/or handling prior to use.

In view of the above, new methods for incorporating insoluble or difficult-to-solubilize biocides into plastics resins that avoid the settling and/or viscosity increase problems of the prior art compositions would be highly desired by the plastics manufacturing community.

SUMMARY OF THE INVENTION

In one aspect, the present invention relates to a multi-step process for preparing a storage-stable dispersion of a biocide which comprises the steps of:

(a) contacting a solid heat swellable resin selected from the group consisting of vinyl polymers with a liquid carrier selected from the group consisting of phthalic acid derivatives to provide a mixture of said resin and said carrier, (b) heating said mixture to an elevated temperature to cause the resin to swell by virtue of carrier absorption into the resin to provide a swelled resin mixture, and (c) adding a solid biocide to said swelled resin mixture and mixing to provide a homogeneous, storage stable solid-liquid dispersion.

In another aspect, the present invention relates to a process for preparing a storage stable liquid dispersion of a biocide which comprises the steps of:

(a) heating a mixture of a biocide, a carrier and a heat swellable polymer to an elevated temperature of between about 50° C. and about 120° C. (preferably between about 70° C. and about 110° C.) to cause said polymer to swell by carrier absorption into said polymer thereby providing a swelled polymer plus biocide mixture characterized by an increased viscosity sufficient to render said swelled polymer plus biocide mixture storage stable, and (b) cooling said swelled polymer plus biocide mixture to a temperature of between about −20° C. and about 40° C. to provide a storage-stable mixture having a viscosity of between about 2,000 and about 30,000 (preferably between about 5,000 and about 15,000) centipoise.

In yet another aspect, the present invention relates to the storage-stable compositions produced by above processes.

These and other aspects will become apparent upon reading the following detailed description of the invention.

DETAILED DESCRIPTION OF THE INVENTION

In accordance with the present invention, it has now been surprisingly found that storage-stable dispersions of solid biocides in swellable polymer resins are provided by causing carrier absorption into the polymer to occur under elevated temperature conditions. The resulting dispersions are storage-stable against settling and against "setting-up" that would otherwise typically occur during warehousing of the dispersions prior to use.

Carriers useful in the process of the present invention include, for example, plasticizers and other resin-compatible additives. Useful plasticizer-type carriers include, for example, adipic acid derivatives such as diisobutyl adipate, di-n-hexyl adipate, heptyl nonyl adipate, bis(2-ethylhexyl) adipate, diisodecyl adipate and bis(2-butoxyethyl)adipate; azelaic acid derivatives such as bis(2-ethylhexyl) azelate; benzoic acid derivatives such as diethylene glycol dibenzoate, dipropyleneglycol dibenzoate, and 2,2,4-trimethyl-1,3-pentanediol-isobutyrate benzoate; citric acid derivatives such as tri-n-butyl citrate and tri-n-butyl acetylcitrate; epoxy derivatives such as epoxidized soybean oil, epoxidized linseed oil, 2-ethylhexyl epoxy tallate and bisphenol A diglycidyl ether; glycol derivatives such as diethlyene glycol dipelargonate, triethylene glycol di-2-ethylbutyrate, and poly(ethylene glycol) (200) di-2-ethylhexanoate; glycolates such as methyl phthalyl ethyl glycolate and butylphthalyl ethyl glycolate; hydrocarbons such as hydrogenated terphenyls HB-40, poly(alkyl naphthalenes) Panaflex, aliphatic aromatics [LEROMOLL] and chlorinated paraffin (52% wt % Cl ) [CERECLOR S-52]; isophthalic acid derivatives such as di-2-ethylhexyl isophthalate; oleic acid derivatives such as butyl oleate; phosphoric acid derivatives such as tributyl phosphate, tri-2-ethylhexyl phosphate, tributoxyethyl phosphate, chlorinated diphosphate [PHOSGARD 2XC-20], cresyl diphenyl phosphate, tricresyl phosphate, isopropylphenyl diphenyl phosphate [KROTINEX 100], t-butylphenyl diphenyl phosphate [SANTICIZER 154], 2-ethylhexyl diphenyl phosphate and isodecyl phosphate; phosphoric acid derivatives such as chlorinated polyphosphonate [PHOSGARD C-22-R]; phthalic acid derivatives such as dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_{7-C_{11}}$) mixed linear phthalates [SANTICIZER 711 or PLATINOL 711P], bis(2-ethylhexyl)phthalate, (n-hexyl, n-octyl, n-decyl) phthalate, (n-octyl, n-decyl) phthalate, diisodecyl phthalate, diundecyl phthalate, ditridecylphthalate, butyl cyclohexyl phthalate, butyl benzyl phthalate, 7-(2,6,6,8-tetramethyl-4-oxa-3-oxo-nonyl)benzyl phthalate, bis(2-butoxyethyl) phthalate and dicylclohexyl phthalate; polyesters such as adipic acid polyester (mol wt 6000) [PARAPLEX G-40], adipic acid polyester (mol wt 2000) [SANTICIZER 334F], azelaic acid polyester (mol wt 850) [PLASTOLEIN 9720], azelaic acid polyester (mol wt 2200) [PLASTOLEIN 9750] and sebacic acid polyester; ricinoleic acid derivatives such as methyl ricinoleate, n-butyl acetylricinoleate and castor oil (90 wt % glyceryl ricinoleate); sebacic acid derivatives such as bis(2-ethylhexyl)sebacate; stearic acid derivatives such as butyl acetoxystearate; sucrose derivatives such as sucrose acetate-isobutyrate; sulfonic acid derivatives such as N-thyl-(o,p)-toluenesulfonamide and alkylsulfonic acid ester of phenol and cresol [MESAMOLL]; terephthalic acid derivatives such as bis(2-ethylhexyl) terephthalate; and trimellitic acid derivatives such as tris(2-ethylhexyl) trimellitate, heptyl nonyl trimellitate, heptyl nonyl undecyl trimellitate and triisodecyl trimellitate.

Other useful carriers include additives not normally classified as plasticizers, such as polyols. An important criterion for the additive(s) useful as carriers within the scope of the present invention is that the additive(s) interacts with the selected swellable polymer resin upon heating to cause swelling of the polymer particles. In order for the carrier to be useful in a specific application, swelling of the polymer particles must occur at an elevated temperature below the degradation temperature of the polymer and of the carrier. Heat stabilizers can optionally be employed.

The amount of carrier employed in the processes of the present invention suitably ranges between about 20 and about 95, preferably between about 50 and about 85, weight percent based upon the total weight of the dispersion.

Suitable heat swellable polymer resins useful in the present invention include, for example, the following resins and combinations thereof: cellulosics such as cellulose acetate, cellulose acetate-butyrate, cellulose nitrate, and ethylcellulose; polyacrylates such as poly(methyl methacrylate) and acrylic copolymers, polystyrenes; polyolefins such as polyethylene and polypropylene; polycarbonates; rubbers and synthetic elastomers; vinyl polymers such as poly(vinyl acetate), poly(vinyl butyral), poly(vinyl alcohol) and poly(vinylchloride); and polyacrylonitrile and modified copolymers thereof; and combinations thereof. The degree of crystallinity of any particular polymer may affect the extent of carrier absorption into the polymer for the specific carrier selected, as would be readily apparent to those of ordinary skill in the art.

The amount of swellable polymer resin(s) employed in the processes of the present invention suitably ranges between about 5 and about 50, preferably between about 5 and about 30, weight percent based upon the total weight of the dispersion.

Suitable biocides useful in the present invention include, for example, the following biocides and combinations thereof:

OBPA —10,10'-oxybisphenoxarsine

VANCIDE 89— N-(trichloromethylthio)-4-cyclohexene-1,2-dicarboximide
DOWCIL A-40-2,3,5-trichloro-4-propylsulfonyl pyridine
zinc OMADINE®—zinc salt of 1-hydroxypyridine-2-thione sodium OMADINE—sodium salt of 1-hydroxypyridine-2-thione
chitosan OMADINE—chitosan pyrithione FUNGITROL 11—N-(trichloromethylthio)phthalimide N-(2-methylnaphthyl)maleimide
DIFOLATAN—cis-N-(1,1,2,2-tetrachloroethyl)-thio-4-cyclohexene-1,2-dicarboximide
ISOLAN—1-isopropyl-3-methyl pyrazolyl-5-dimethyl carbamate 3-methyl-pyrazolyl dimethylcarbamate
MANEB—manganese ethylene bisdithiocarbamate
ZINEB—zinc analog of Maneb
NABAM—disodium analog of Maneb
FERBAM—ferric dimethyl dithiocarbamate
ZIRAM—zinc analog of Ferbam
XARATHANE—2,4-dinitro-6-capryl phenol crotonate
OVATRAN—p-chlorophenyl-p-chlorobenzenesulphonate
SKANE M-8—2-N-octyl-4-isothiazolin-3-one
Benomyl-methyl-l(butylcarbamoyl)-2-benzimidazole carbamate
METASOL TK-100—2(4-thiazolyl)benzimidazole
Copper-8—copper 8-hydroxy-quinolinate
a-diethoxyphosphinodithioacetylurea
a-dimethoxyphosphinodithioacetylurea
Diethoxyphosphinodithioacetamide
Dimethoxyphosphinodirhioacetamide
Bis(dimethylamido)phosphoryl fluoride
Tributyl tin fluoride
2-cyclohexyl-3-isothiazolone
4,5-dichloro-2-cyclohexyl-3-isothiazolone and mixtures thereof.

The preferred biocides are sodium pyrithione, zinc pyrithione, chitosan pyrithione, and combinations thereof.

The biocide(s) is typically employed in an amount of between about one and about 30, preferably between about 5 and about 20, weight percent based upon the total weight of the dispersion. The processes of the present invention are suitable for the preparation of resin concentrates, if desired, containing high levels of biocide. The concentrates are subsequently diluted with additional polymer resin, which can be the same or different resin from that used in the preparation of the concentrate, to provide a working composition containing at least a "biocidally effective amount" of biocide, i.e., an amount of biocide sufficient to provide the desired level of biocidal efficacy in the working composition. Selection of the carrier for use in the preparation of a concentrate advantageously takes into account additives that are desirably present in the working composition. Alternatively, the working composition is suitably prepared directly using the processes of the present invention without the necessity for preparing a concentrate. The processes of the present invention are suitably effected in a few minutes or less up to ten hours or more, depending upon the specific starting materials and processing conditions employed.

Other additives are suitably optionally employed in the processes of the present invention, including for example pigments such as titanium dioxide, fillers and reinforcing agents such as glass fibers, heat stabilizers such as calcium sterate, uv stabilizers, surfactants such as polyalkyleneoxide ethers, and the like, and combinations thereof. If used, the optional additives are suitably employed in a minor amount of less than fifty weight percent based upon the weight of the polymer resin.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

Part A—Preparation of a preliminary Zinc Pyridinethione/ Plasticizer Dispersion

Butylbenzylphthalate (BBP) (2400 grams) was added to wet zinc pyridinethione filter cake (1201.8 grams) in a stainless steel beaker and mixed on a high speed disperser until smooth (approx. one hour). The mixture was transferred to a five liter glass round bottom flask for vacuum water removal. The mixture was stirred under vacuum as heat was slowly applied using a heating mantle. The temperature rose slowly as the water was removed. The process was halted when the temperature reached 91° C. The mixture was then cooled to about 28° C. using a water bath to provide a preliminary dispersion which was not storage stable. This dispersion was analyzed to contain 21.2% zinc pyridinethione and less than 0.25% water.

Part B—Preparation of a 5% Zinc Pyridinethione Dispersion Containing 14% PVC Prepared at an Elevated Temperature Zinc pyridinethione dispersion (117.9 grams; 21.2% active in BBP), prepared in accordance with Part A above, was combined with BF Goodrich GEON 125A PVC (70.0 grams) and BBP (312.1 grams). Stirring was continued throughout the reaction. The mixture was warmed to 80° C. using an oil bath. The temperature was maintained for 5 hours. The heat was removed, the mixture was allowed to air cool 15 minutes, and then cooled further using tap water until temperature drops to 30° C. The resulting dispersion containing 5% zinc pyridinethione and 14% PVC was stable at room temperature and had a static viscosity of approx. 22,000 cps at 20° C.

Comparative Example A

Part A—Preparation of PVC-Butylbenzylphthalate Plastisol

Borden VC440 (Plastisol grade PVC; 70 grams) was mixed with BBP (30 grams) until smooth and uniform. This formulation yielded a very thick plastisol similar to those commercially available.

Part B—5.0% Zinc Pyridinethione in 52.6% PVC Plastisol

Zinc pyridinethione preliminary dispersion from Example 1, Part A (13.2 grams, 20.15% active in BBP) was added to the PVC plastisol (40 grams) from Part A of this Comparative Example and mixed well. The resulting formulation, prepared using typical plastisol technology, was stable at room temperature, but storage overnight at 50° C. yielded an unacceptable solid mass.

EXAMPLE 2

Effect of Temperature on Viscosity for a 5% Zinc Pyridinethione Dispersion Containing 14% PVC Utilizing a procedure analogous to the procedure of Example 1, a sample of the dispersion from Part B of Example 1 (aged 6 days) was equilibrated to a series of temperatures starting at 20° C. and ranging up to 60° C. and back, at five degree increments. The viscosity was measured using a Brookfield viscometer at each temperature with and without stirring. After the measurement, the same sample was equilibrated to the next higher temperature and the measurement repeated.

The results of these measurements indicated that the viscosity dropped relatively rapidly from 20° C. to 40° C. (>22,000 cps to >4,000 cps, respectively). The viscosity then gradually dropped to about 2,000 cps at 60° C. The viscosity of the sample returned to near its initial value when the sample was cooled back to 25° C. (16,000–18,000 cps). Note that this behavior was directly opposite to that typically exhibited by standard plastisols which generally become irreversibly thick at increased temperatures as illustrated by Comparative Example A.

EXAMPLE 3

Processing Time and PVC Level Effect on the Viscosity of a 5% Zinc Pyridinethione Dispersion A series of dispersions were prepared following the procedure of Example 1 by combining Zinc Pyridinethione preliminary dispersion (125.7 grams; 19.9% active in BBP) with BF Goodrich GEON 125A Plastisol grade PVC and BBP. The amounts of PVC and BBP for each formulation were as follows:

| Formulation | PVC (grams) | BBP (grams) |
| --- | --- | --- |
| Sample A | 65 | 309.3 |
| Sample B | 70 | 304.3 |
| Sample C | 75 | 299.3 |
| Sample D | 80 | 294.3 |

Stirring was continued throughout the reaction. The mixture was warmed to 80° C. using an oil bath. Aliquots of each Sample were taken at hourly intervals in order to make viscosity measurements. The dispersion viscosity was found to increase with time for each Sample. Also, viscosity was found to be a direct function of polymer concentration.

EXAMPLE 4

Preparation of 5% Zinc Pyridinethione Dispersions in a Mixed Dialkylphthalate Carrier A series of dispersions were prepared following the procedure of Example 1 by combining Zinc pyridinethione preliminary dispersion (22.45% active in Platinol 711P [Dialkyl ($C_7C_9C_{11}$) Mixed Linear Phthalate] with BF Goodrich GEON 125A Plastisol grade PVC and Platinol 711P. These formulations were heated using an oil bath to a series of temperatures for four hours. The processing temperature, amounts of zinc pyridinethione concentrate, PVC and Platinol 711P for each formulation are as follows:

| Formulation | Zinc Pyridinethione Preli.Dispers. (grams) | PVC (grams) | Platinol 711P (grams) | Temp. (C.) |
| --- | --- | --- | --- | --- |
| Sample E | 111.6 | 100 | 288.4 | 80 |
| Sample F | 111.6 | 125 | 263.4 | 90 |
| Sample G | 223.2 | 100 | 676.8 | 100 |

All dispersions identified as Samples E through G were found to have acceptable viscosities ranging from approx. 6,000–approx. 8,000 cps. As expected, higher polymer levels were required at lower processing temperatures to achieve similar viscosities.

EXAMPLE 5

5% Pyridinethione Dispersions in Dioctylphthalate (DOP) Carrier

A series of dispersions were prepared following the procedure of Example 1 by combining Zinc pyridinethione preliminary dispersion (21.0% active in DOP) with BF Goodrich GEON 125A Plastisol grade PVC and DOP. These formulations were heated using an oil bath to a series of temperatures for four hours. The processing temperature, amounts of zinc pyridinethione concentrate, PVC and DOP for each formulation are as follows:

| Formulation | Zinc Pyridinethione Preli.Dispers. (grams) | PVC (grams) | DOP (grams) | Temp. (C.) |
|---|---|---|---|---|
| Sample H | 142.86 | 108 | 349.14 | 80 |
| Sample I | 119.05 | 60 | 320.95 | 90 |

EXAMPLE 6

5% Zinc Pyridinethione Dispersions in Epoxidized Soybean Oil (ESO) Carrier

A series of dispersions were prepared following the procedure of Example 1 by combining Zinc pyridinethione preliminary dispersion (140.2 grams; 21.4% active in ESO) with BF Goodrich GEON 125A Plastisol grade PVC and ESO. The dispersion was heated using an oil bath to 80° C. for four hours.

This dispersion had an initial viscosity of approx. 6,000 cps. which, after 4 weeks, increased to approx. 11,000 cps. which is well within acceptable limits.

EXAMPLE 7

The Effect of Stirring

A sample, prepared using the procedure described in Example 1 but using the following: 15% GEON 125A PVC, heated at 80° C. for 5 hours, had a viscosity of approx. 15,000 cps. A similarly prepared formulation, stirred for 3 days at ambient temperature had a viscosity of less than 4,000 cps. Thus, stirring can be used to provide dispersions which have lower viscosities than otherwise would be obtained.

What is claimed is:

1. A process for preparing a storage stable dispersion of a solid biocide which comprises the steps of:

(a) forming a preliminary dispersion by mixing a solid biocide dispersed in water and a carrier selected from the group consisting of phthalic acid derivatives to form an aqueous biocide/plasticizer mixture, and heating said aqueous biocide/plasticizer mixture under vacuum to remove water therefrom, thereby forming a water-free preliminary dispersion of biocide in plasticizer, (b) heating a mixture of said preliminary dispersion, additional carrier selected from the group consisting of phthalic acid derivatives and a heat swellable polymer selected from the group consisting of vinyl polymers to an elevated temperature of between about 50° C. and about 120° C. to cause said polymer to swell by carrier absorption into said polymer thereby providing a swelled polymer plus biocide mixture characterized by an increased viscosity sufficient to render said swelled polymer plus biocide mixture storage stable, and (c) cooling said swelled polymer plus biocide mixture to a temperature of between about −20°C. and about 40° C. to provide a storage-stable dispersion having a viscosity of between about 2,000 and about 30,000 centipoise, said carrier being employed in an amount of between about 20 and about 95 weight percent based upon the total weight of the dispersion.

2. The process of claim 1 wherein said biocide is selected from the group consisting of sodium pyrithione, zinc pyrithione, chitosan pyrithione, and combinations thereof.

3. The process of claim 1 wherein said biocide is employed in an amount of between about 1 and about 30 weight percent based upon the total weight of the dispersion.

4. The process of claim 1 wherein said heat-swellable polymer is polyvinyl chloride.

5. The process of claim 1 wherein said heat swellable polymer is selected from the group consisting of: poly(vinyl acetate), poly(vinyl butyral), poly(vinyl alcohol), and poly(vinylchloride), and combinations thereof.

* * * * *